(12) United States Patent
Marengo et al.

(10) Patent No.: US 9,845,481 B2
(45) Date of Patent: *Dec. 19, 2017

(54) SYNTHETIC REGULATION OF GENE EXPRESSION

(71) Applicant: Duke University, Durham, NC (US)

(72) Inventors: Matthew S. Marengo, Durham, NC (US); Mariano A. Garcia-Blanco, Hillsborough, NC (US)

(73) Assignee: Duke University, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/055,880

(22) Filed: Feb. 29, 2016

(65) Prior Publication Data

US 2016/0281107 A1 Sep. 29, 2016

Related U.S. Application Data

(63) Continuation of application No. 13/783,450, filed on Mar. 4, 2013, now Pat. No. 9,284,575.

(60) Provisional application No. 61/607,312, filed on Mar. 6, 2012.

(51) Int. Cl.

| *C12P 21/06* | (2006.01) |
| *C12N 15/85* | (2006.01) |
| *C12N 5/04* | (2006.01) |
| *C12N 5/07* | (2010.01) |
| *C12N 15/00* | (2006.01) |
| *C12N 15/09* | (2006.01) |
| *C12N 15/11* | (2006.01) |
| *C12N 15/12* | (2006.01) |
| *C12N 15/29* | (2006.01) |
| *C12N 15/82* | (2006.01) |

(52) U.S. Cl.
CPC .......... *C12N 15/85* (2013.01); *C12N 2800/30* (2013.01); *C12N 2830/008* (2013.01); *C12N 2840/007* (2013.01)

(58) Field of Classification Search
None
See application file for complete search history.

(56) References Cited

U.S. PATENT DOCUMENTS

| 5,097,025 | A | 3/1992 | Benfey et al. |
| 5,880,330 | A | 3/1999 | Weigel et al. |
| 5,981,727 | A | 11/1999 | Baden et al. |
| 6,291,666 | B1 | 9/2001 | Puthigae et al. |
| 7,132,526 | B2 | 11/2006 | Liu et al. |
| 7,323,622 | B2 | 1/2008 | Mirkov et al. |
| 7,557,264 | B2 | 7/2009 | Allen et al. |
| 9,284,575 | B2 * | 3/2016 | Marengo ................ C12N 15/85 |
| 2005/0034192 | A1 | 2/2005 | Damaj et al. |
| 2005/0086712 | A1 | 4/2005 | Meyer et al. |
| 2007/0180580 | A1 | 8/2007 | Hertzberg |
| 2010/0269226 | A1 | 10/2010 | Hehl et al. |

FOREIGN PATENT DOCUMENTS

WO   WO 2011/003901   1/2011

OTHER PUBLICATIONS

Baraniak, A.P., et al., "Fox-2 Mediates Epithelial Cell-Specific Fibroblast Growth Factor Receptor 2 Exon Choice." Molecular and Cellular Biology Feb. 2006, p. 1209-1222.
Barash, Y., et al., "Model-based detection of alternative splicing signals." Bioinformatics 2010, 26(12):i325-33.
Black, D.L., "Activation of c-src neuron-specific splicing by an unusual RNA element in vivo and in vitro." Cell. May 29, 1992; 69(5):795-807.
Black, D.L.,, "Mechanisms of Alternative Pre-Messenger RNA Splicing." Annu. Rev. Biochem. 2003, 72:291-336.
Carstens, R.P., et al., "An intronic splicing silencer causes skipping of the IIIb exon of fibroblast growth factor receptor 2 through involvement of polypyrimidine tract binding protein." Mol Cell Biol. Oct. 2000; 20(19):7388-400.
Chan, R.C., and Black, D.L., "Conserved Intron Elements Repress Splicing of a Neuron-Specific c-src Exon In Vitro." Mol. Cell. Biol. Nov. 1995, 15(11):6377-6385.
Chan, R.C. and Black, D.L., "The Polypyrimidine Tract Binding Protein Binds Upstream of Neural Cell-Specific c-src Exon N1 to Repress the Splicing of the Intron Downstream." Mol. Cell. Biol. Nov. 1997, 17(8):4667-4676.
Gallego, M.E., et al., "Tissue-specific splicing of two mutually exclusive exons of the chicken beta-tropomyosin pre-mRNA: positive and negative regulations." Biochimie. 1996;78(6):457-65.
Gallo, J., and Spickett, C., "The role of CELF proteinsin neurological disorders." RNA Biology, Jul./Aug. 2010, 7:4:474-479.
Garcia-Blanco, M.A., et al., Alternative splicing in disease and therapy, Nature biotechnology, 2004, pp. 535-546, vol. 22:2.
Gooding, C. and Smith, C.W.J., "Tropomyosin exons as models for alternative splicing." Adv Exp Med Biol. 2008;644:27-42.
Human FoxJ1 Antibody Datasheet, R&D Systems, 2011.
Kornblihtt, A.R., et al., "The fibronectin gene as a model for splicing and transcription studies." The FASEB Journal Feb. 1996, 10:248-57.
Ladd, A.N., et al., "The CELF Family of RNA Binding Proteins Is Implicated in Cell-Specific and Developmentally Regulated Alternative Splicing." Mol Cell Biology, Feb. 2001, p. 1285-1296.
Li, C.S, et al., Identification of single nucleotide polymorphisms in FOXJ1 and their association with allergic rhinitis, J Hum Genet, 2006, pp. 292-297, vol. 51.
Mankodi, A. et al., "Expanded CUG Repeats Trigger Aberrant Splicing ofC1C-1 Chloride Channel Pre-mRNA and Hyperexcitability of Skeletal Muscle in Myotonic Dystrophy." Molecular Cell Jul. 2002, 10: 35-44.

(Continued)

*Primary Examiner* — Nancy J Leith
(74) *Attorney, Agent, or Firm* — Andrus Intellectual Property Law, LLP

(57) ABSTRACT

Synthetic regulation of gene expression is provided. In some embodiments, synthetic regulatory constructs are provided. In some embodiments, a synthetic regulatory construct expresses a heterologous gene in a selected cell type. In some embodiments, methods of expressing a heterologous gene in a selected cell type are provided.

22 Claims, 7 Drawing Sheets

(56) References Cited

OTHER PUBLICATIONS

Min, H., et al., "A new regulatory protein, KSRP, mediates exon inclusion through an intronic splicing enhancer." Genes & Dev. 1997, 11:1023-1036.
Oltean, S., et al., "Dunning rat prostate adenocarcinomas and alternative splicing reporters: powerful tools to study epithelial plasticity in prostatetumors in vivo" Clin Exp Metastasis 2008, 25(6): 611-9.
Ostrowski, L.E., et al., Targeting expression of a Transgene to the airway surface epithelium using a ciliated cell-specific promoter, Molecular Therapy, 2003, pp. 637-645, vol. 8:4.
Philips, A.V., et al., "Disruption of Splicing Regulated by a CUG-Binding Protein in Myotonic Dystrophy." Science 1998, 280: 737-741.
Ranum, L.P.W., and Cooper, T.A., "RNA-MediatedNeuromuscular Disorders." Annu. Rev. Neurosci. 2006. 29:259-77.
Reddy, A.S.N., Alternative splicing of pre-messenger RNAs in plants in the genomic era, Annu. Rev. Plant Biol., 2007, pp. 267-294, vol. 58.
Savkur, R.S., et al., "Aberrant regulation of insulin receptor alternative splicing is associated with insulin resistance in myotonic dystrophy." Nat. Gen. Sep. 2001, 29: 40-47.

Seth, P., et al., "Identification of an Intronic Splicing Enhancer Essential forthe Inclusion of FGFR2 Exon IIIc." J. Biol. Chem., Apr. 11, 2008, 283(15): 10058-10067.
Tennant, T.R., et al., "The Dunning model." Prostate. Jun. 1, 2000; 43(4):295-302.
Ule, J., et al., "An RNA map predicting Nova-dependent splicing regulation." Nature. Nov. 30, 2006; 444(7119):580-6.
Wang, Y., et al., Transcriptional regulation of co-expressed microRNA target genes, Genomics, 2011, pp. 445-452, vol. 98.
Warzecha, C.C., et al., "ESRP1 and ESRP2 are epithelial cell type-specific regulators of FGFR2 splicing." Mol Cell. Mar. 13, 2009; 33(5): 591-601.
Warzecha, C.C., et al., "The epithelial splicing factors ESRP1 and ESRP2 positively and negatively regulate diverse types of alternative splicing events." RNA Biol. 2009, 6(5): 546.
Yeo, G.W., et al., "An RNA code for the FOX2 splicing regulator revealedby mapping RNA-protein interactions in stem cells." Nature Structural & Molecular Biology, 2009, 16(2): 130-137.
Yeo, J. et al., "RNA editing changes the lesion specificity for the DNA repair enzyme NEIL1." Proc Natl Acad Sci U S A. Nov. 30, 2010; 107(48):20715-9.

\* cited by examiner mesenchymal epithelial

FIGURE 2, Cont.

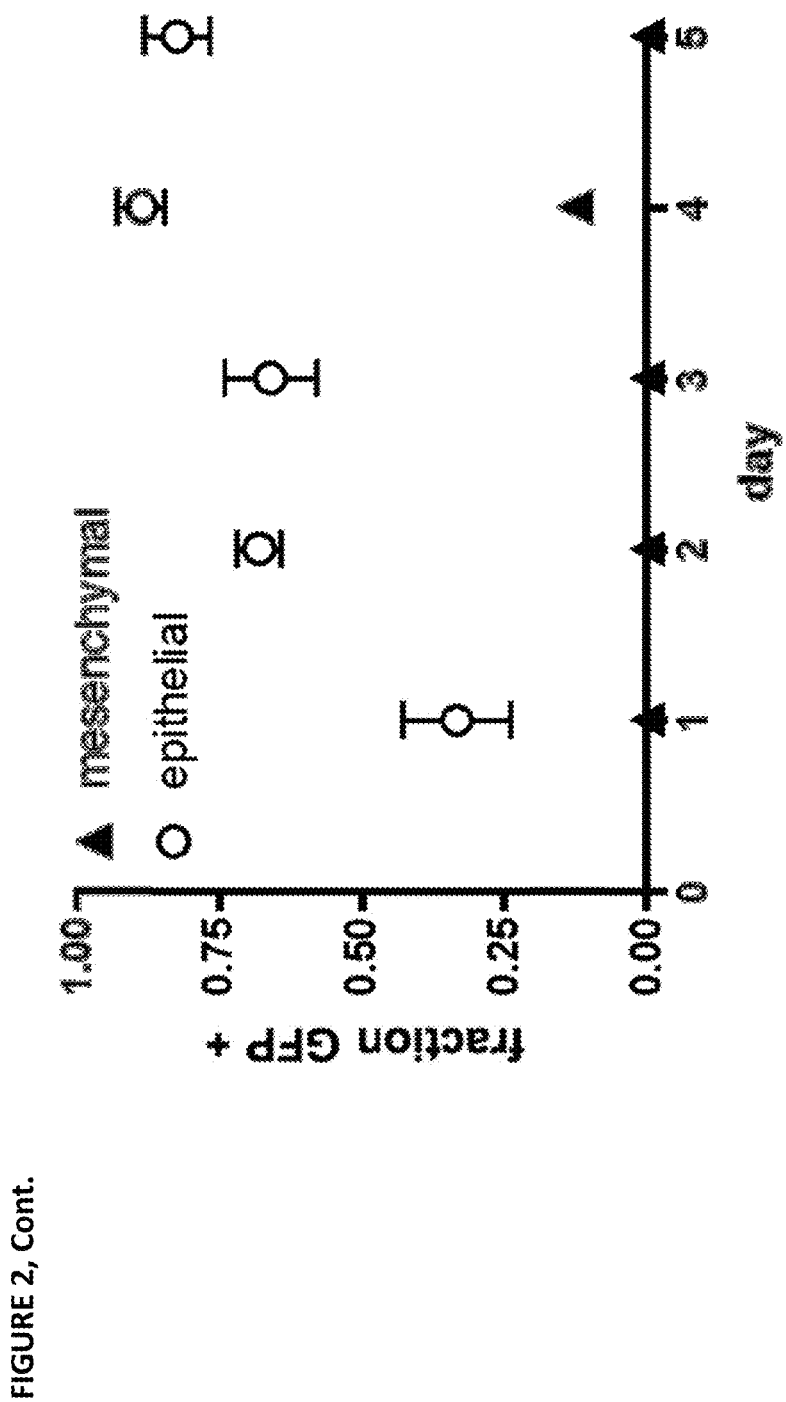
FIGURE 2, Cont.

FIGURE 4, Cont.

SYNTHETIC REGULATION OF GENE EXPRESSION

This application is a continuation application of U.S. application Ser. No. 13/783,450 filed Mar. 4, 2013, which claims the benefit of U.S. Provisional Application No. 61/607,312, filed Mar. 6, 2012, both of which are incorporated herein by reference in their entirety for any purpose.

STATEMENT REGARDING FEDERALLY SPONSORED RESEARCH

This invention was made with government support under Federal Grant Nos. IF32CA142095 and R01CA127727, both awarded by the National Institutes of Health: National Cancer Institute. The government has certain rights in the invention.

BACKGROUND

Current work in synthetic biology is focused on modifying protein structure and function, and regulation of gene expression circuits at the level of transcription promoters (Kwok, 2010). While promoter control of expression may be sufficiently specific in bacterial systems, heterologous promoters confer only limited control of gene expression (e.g. cell-specific expression) in eukaryotic cells, possibly because of a lack of correct chromatin assembly (Wolffe, 1999). The limited control of gene expression in eukaryotic cells by heterologous promoters alone may be insufficient for certain therapies and other biotechnological applications. Complete spatiotemporal control of gene expression is important for the use of at least a subset of biological molecules in gene therapy and other biotechnological applications.

SUMMARY

In some embodiments, synthetic regulatory constructs are provided. In some embodiments, a synthetic regulatory construct comprises a cell-specific promoter, a heterologous gene, and a cell-specific exon. In some embodiments, the cell-specific exon is excluded in the cell in which the cell-specific promoter is most active. In some embodiments, inclusion of the exon results in the product of the heterologous gene being inactive, or no product of the heterologous gene being produced. In some embodiments, inclusion of the exon results in a frame shift in the heterologous gene or a stop codon before or within the heterologous gene, or both.

In some embodiments, the cell-specific exon is included in the cell in which the cell-specific promoter is most active. In some embodiments, exclusion of the exon results in the product of the heterologous gene being inactive, or no product of the heterologous gene being produced. In some embodiments, exclusion of the exon results in a frame shift in the heterologous gene or a stop codon before or within the heterologous gene, or both.

In some embodiments, a synthetic regulatory construct comprises a cell-specific RNA stability element. In some such embodiments, the cell-specific RNA stability element is a microRNA target sequence.

In some embodiments, a cell-specific promoter is at least 2-fold, at least 3-fold, at least 5-fold, at least 7-fold, or at least 10-fold more active in a selected cell than in at least one other cell comprised in the same organism as the selected cell. In some embodiments, a cell-specific promoter is at least 2-fold, at least 3-fold, at least 5-fold, at least 7-fold, or at least 10-fold more active in a selected cell than in at least two, at least three, or at least five other cells comprised in the same organism as the selected cell. In some embodiments, a cell-specific promoter is at least 2-fold, at least 3-fold, at least 5-fold, at least 7-fold, or at least 10-fold more active in a selected cell than in any other cell comprised in the same organism as the selected cell.

In some embodiments, a cell is an animal cell. In some embodiments, a cell is a mammalian cell. In some embodiments, the mammal is selected from human, mouse, rat, dog, chimpanzee, and monkey. In some embodiments, a cell is a plant cell. In some embodiments, a plant is selected from a monocot and a dicot. In some embodiments, a cell is a fungal cell.

In some embodiments, cells comprising synthetic regulatory constructs are provided. In some embodiments, a cell is an animal cell. In some embodiments, a cell is a mammalian cell. In some embodiments, a cell is comprised in a mammal. In some embodiments, a cell is ex vivo or in vitro. In some embodiments, a cell is a plant cell. In some embodiments, a cell is comprised in a plant. In some embodiments, a cell is a fungal cell.

In some embodiments, methods of expressing a heterologous gene in a selected cell are provided. In some embodiments, a method comprises introducing a synthetic regulatory construct into the selected cell. In some embodiments, a cell is an animal cell. In some embodiments, a cell is a mammalian cell. In some embodiments, the mammal is selected from human, mouse, rat, dog, chimpanzee, and monkey. In some embodiments, a selected cell is selected from mesenchymal, epithelial, neuronal, heart muscle, skeletal muscle, smooth muscle, and embryonic muscle cells. In some embodiments, a cell is comprised in a mammal. In some embodiments, a cell is a plant cell. In some embodiments, a cell is comprised in a plant. In some embodiments, a cell is a fungal cell.

DETAILED DESCRIPTION

Figure 1A:
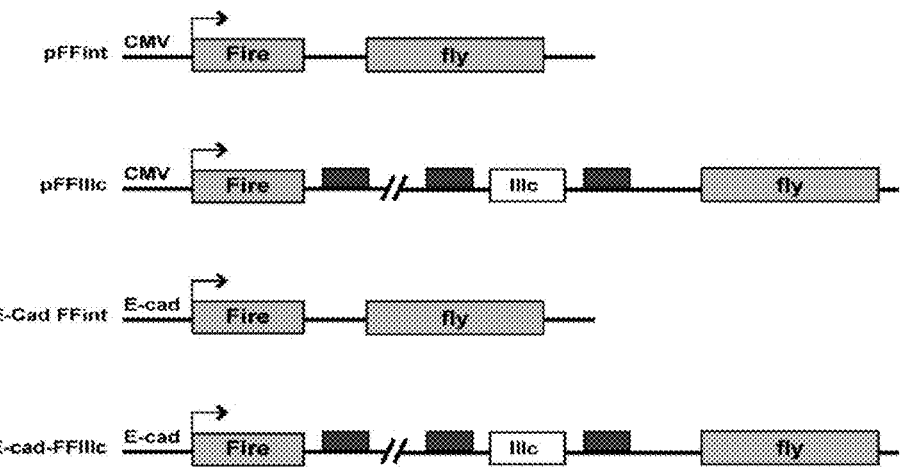
FIG. 1 shows in FIG. 1A schematic diagrams of four plasmids with various elements for synthetic regulation of firefly luciferase expression, and in FIG. 1B expression of firefly luciferase in mesenchymal and epithelial cells transfected with the plasmids from FIG. 1A, as described in Example 1.

The present inventors have developed a synthetic gene regulation system that provides better spatiotemporal regulation than promoters used alone. In some embodiments, the synthetic gene regulation system described herein provides better cell-specificity than cell-specific promoters used alone. In some embodiments, the synthetic gene regulation system described herein provides better temporal regulation than certain promoters used alone. In some embodiments, the synthetic gene regulation system may be used for cell-specific and/or temporal regulation of expression of various agents, including, but not limited to, therapeutic agents. Accordingly, in some embodiments, artificial control of the expression of biological molecules, including, but not limited to, therapeutic biological molecules, via combinations of cell-specific promoters, cell-specific exons and cell-specific RNA stability elements, is provided. In some embodiments, artificial control of the expression of biological molecules, including, but not limited to, therapeutic biological molecules, via combinations of temporally-regulated promoters, temporally-regulated exons and temporally-regulated RNA stability elements, is provided. In some embodiments, such modular regulatory elements may come from different genes or be artificial combinations of known sub-elements.

As described herein, post-transcriptional regulation offers additional control of gene expression, particularly in eukaryotic cells. For example, in some embodiments, alternative cassette exons may either be included or skipped in eukaryotic mRNA in a cell-specific manner ("cell-specific exons"). In some embodiments, alternative exon inclusion may disrupt the expression of, or change the function of, a gene product. Like transcription promoters, exons are recognized by regulatory macromolecular complexes in the cell. Further, this recognition may be modular: exons may be moved into heterologous contexts and still be recognized by the cell.

As a further example, in some embodiments, post-transcriptional regulation can determine the stability of mRNAs in a cell-specific manner ("cell-specific RNA stability elements"). In some embodiments, by affecting RNA stability, such post-transcriptional regulators may determine RNA levels. This regulation may also be accomplished by an independent set of macromolecular complexes. In some embodiments, regulation of RNA stability involves small non-coding RNAs known as microRNAs (miRNAs). In some embodiments, mRNAs may be regulated at the level of translation efficiency, for example, by proteins and miRNAs, which may exert their function via signals in the 5' and/or 3' untranslated regions (UTRs) of the messenger.

As discussed herein, in some embodiments, the various levels of regulation (including, but not limited to, transcription, alternative splicing, and RNA stability) are orthogonal and thus provide independent modes that in combination provide multiplied specificity. Thus, in some embodiments, by combining modular control elements from different genes, novel or artificially stringent patterns of gene expression can be engineered. Currently, such modular control does not appear to be appreciated in synthetic biology.

Definitions

The subject matter disclosed herein is described using several definitions, as set forth below and throughout the application.

Unless otherwise noted, the terms used herein are to be understood according to conventional usage by those of ordinary skill in the relevant art. In addition to the definitions of terms provided below, it is to be understood that as used in the specification, embodiments, and in the claims, "a", "an", and "the" can mean one or more, depending upon the context in which it is used.

As used herein, "about," "approximately," "substantially," and "significantly" will be understood by persons of ordinary skill in the art and will vary to some extent on the context in which they are used. If there are uses of the term which are not clear to persons of ordinary skill in the art given the context in which it is used, "about" or "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising."

As used herein, the term "cell-specific promoter" refers to a promoter that is at least 3-fold more active in a selected cell than in one or more other cells. In some embodiments, a cell specific promoter is at least 4-fold, at least 5-fold, at least 6-fold, at least 7-fold, at least 8-fold, at least 9-fold, or at least 10-fold more active in a selected cell than in one or more other cells. In some embodiments, a cell specific promoter is at least 3-fold, at least 4-fold, at least 5-fold, at least 6-fold, at least 7-fold, at least 8-fold, at least 9-fold, or at least 10-fold more active in a selected cell than in other cells found in the same organism as the selected cell. In some embodiments, a selected cell is a particular cell type.

As used herein, the term "cell-specific exon" refers to an exon that is present in a transcript or absent from a transcript through alternative splicing at a rate that is at least 3-fold greater in a selected cell than in one or more other cells. In some embodiments, a cell-specific exon is present in a transcript in a selected cell at a rate that is at least 3-fold, at least 4-fold, at least 5-fold, at least 6-fold, at least 7-fold, at least 8-fold, at least 9-fold, or at least 10-fold greater than it is present in a transcript in one or more other cells. In some embodiments, a cell-specific exon is absent from a transcript in a selected cell at a rate that is at least 3-fold, at least 4-fold, at least 5-fold, at least 6-fold, at least 7-fold, at least 8-fold, at least 9-fold, or at least 10-fold greater than it is absent from a transcript in one or more other cells. In some embodiments, a cell-specific exon is present in a transcript in a selected cell at a rate that is at least 3-fold, at least 4-fold, at least 5-fold, at least 6-fold, at least 7-fold, at least 8-fold, at least 9-fold, or at least 10-fold greater than it is present in a transcript in other cells found in the same organism as the selected cell. In some embodiments, a cell-specific exon is absent from a transcript in a selected cell at a rate that is at least 3-fold, at least 4-fold, at least 5-fold, at least 6-fold, at least 7-fold, at least 8-fold, at least 9-fold, or at least 10-fold greater than it is absent from a transcript in other cells found in the same organism as the selected cell. In some embodiments, a selected cell is a particular cell type.

In some embodiments, the rate that an exon is present is determined as the ratio of spliced transcript with the exon present to spliced transcript with the exon absent in a particular cell. In some embodiments, the rate an exon is absent is determined as the ratio of spliced transcript with the exon absent to spliced transcript with the exon present in a particular cell. As a nonlimiting example, the following table shows hypothetical rates that a hypothetical cell-specific exon A is present in a transcript in hypothetical cells x and y:

|  | Relative amount of transcript with exon A included | Relative amount of transcript with exon A excluded | Rate exon is included | Fold difference in rate of inclusion in cell x versus cell y |
|---|---|---|---|---|
| Cell x | 10 | 2 | 5 | 10-fold |
| Cell y | 5 | 10 | 0.5 | |

As used herein, the terms "exclusion", "excluded", and similar terms, when used in relation to an exon, mean that the rate that an exon is included in a transcript, as described above, is less than 1. Alternatively, the terms "exclusion", "excluded", and similar terms, when used in relation to an exon, mean that the rate that an exon is excluded from a transcript, determined in a similar manner as described above for inclusion of an exon (although with the numerator and denominator reversed), is greater than 1.

As used herein, the terms "inclusion", "included", and similar terms, when used in relation to an exon, mean that the rate that an exon is included in a transcript, as described above, is greater than 1. Alternatively, the terms "inclusion", "included", and similar terms, when used in relation to an exon, mean that the rate that an exon is excluded from a transcript, determined in a similar manner as described above for inclusion of an exon (although with the numerator and denominator reversed), is less than 1.

As used herein, the term "heterologous gene" refers to any gene or coding sequence that is not controlled in its natural state (e.g., within a non-genetically modified cell) by the cell-specific promoter to which it is operably linked in a particular construct, and whose gene, in its natural state, does not contain the cell-specific exon included in the particular construct. In some embodiments, the gene or coding sequence is described as being heterologous to the cell-specific promoter and/or heterologous to the cell-specific exon.

As used herein, the terms "cell-specific RNA stability element" and "cell-specific RNA stability element" refer to a regulatory element, which may be in the 3'-untranslated region or 5'-untranslated region of a transcript, that increases the stability or translation of a transcript in a selected cell and/or decreases the stability or translation of the transcript in one or more cells other than the selected cell, such that the stability or translation of the transcript in the selected cell is at least 2-fold greater than the stability or translation of the transcript in one or more other cells. In some embodiments, the stability or translation of the transcript in the selected cell is at least 3-fold, at least 4-fold, at least 5-fold, at least 6-fold, at least 7-fold, at least 8-fold, at least 9-fold, or at least 10-fold greater than in one or more other cells. In some embodiments, the stability or translation of the transcript in the selected cell is at least 2-fold, 3-fold, at least 4-fold, at least 5-fold, at least 6-fold, at least 7-fold, at least 8-fold, at least 9-fold, or at least 10-fold greater than in other cells found in the same organism as the selected cell. In some embodiments, a selected cell is a particular cell type. In some embodiments, an RNA stability element is an element that decreases the stability or translation of the transcript in one or more cells other than the selected cell. In some embodiments, a cell-specific RNA stability element is a microRNA target sequence. In some embodiments, a cell-specific RNA stability element is a binding site for an hnRNP protein. Nonlimiting exemplary hnRNPs include AUF-1, AUF-2, and HuR.

The term "microRNA target sequence" refers to a RNA stability element that comprises a seed match sequence for a particular microRNA. A seed match sequence is a sequence that is complementary to at least nucleotides 2 to 7 of the microRNA. In some embodiments, a microRNA target sequence comprises a sequence that is complementary to more of the microRNA than just nucleotides 2 to 7. In some embodiments, a microRNA target sequence decreases the stability or translation of a transcript in cells that express the particular microRNA.

Nonlimiting Exemplary Cell-Specific Promoters

Many cell-specific promoters are known in the art. Nonlimiting exemplary mammalian cell-specific promoters have been characterized and used in mice expressing Cre recombinase in a cell-specific manner. Certain nonlimiting exemplary mammalian cell-specific promoters are listed in Table 1.

TABLE 1

| Nonlimiting exemplary cell-specific promoters | | | | | |
|---|---|---|---|---|---|
| Promoter | Cell/tissue specificity | Promoter | Cell/tissue specificity | Promoter | Cell/tissue specificity |
| A930038C07Rik, RIKEN cDNA A930038C07 gene (mouse) | cortex, striatum, and cerebellum | Col2a1, collagen, type II, alpha 1 (mouse) | differentiating chondrocytes, notochord, submandibular glands | GZMB, granzyme B (granzyme 2, cytotoxic T-lymphocyte-associated serine esterase 1) (human) | activated T cells |
| ACTA1, actin, alpha 1, skeletal muscle (human) | adult striated muscle fibers and embryonic striated muscle cells of the somites and heart | Cr2, complement receptor 2 (mouse) | Mature transitional B cells | Grik4, glutamate receptor, ionotropic, kainate 4 (mouse) | area CA3 of the hippocampus |
| Alb, albumin (rat) | Hepatocytes (liver) | Cspg4, chondroitin sulfate proteoglycan 4 (mouse) | NG2 expressing glial cells and vasculature throughout the brain as well as in NG2-expressing cells in other tissues from late embryonic stages (~embryonic day 14) throughout adulthood | HBB, hemoglobin, beta (human) | Erythroid tissues |

TABLE 1-continued

Nonlimiting exemplary cell-specific promoters

| Promoter | Cell/tissue specificity | Promoter | Cell/tissue specificity | Promoter | Cell/tissue specificity |
|---|---|---|---|---|---|
| Alpl, alkaline phosphatase, liver/bone/ kidney (mouse) | embryonic primordial germ cells | Ctgf, connective tissue growth factor (mouse) | Cortex and hippocampus | Hoxb7, homeobox B7 (mouse) | mesonephric duct and its developmental derivatives (the Wolffian duct, the collecting duct epithelium of kidney and ureteral epithelium), ureteric bud and all ureteric bud epithelial cells; low levels of expression in the dorsal root ganglia and the spinal cord |
| Amh, anti-Mullerian hormone (mouse) | testis Sertoli cells | Cyp39a1, cytochrome P450, family 39, subfamily a, polypeptide 1 (mouse) | cortex, hippocampus, striatum, olfactory bulb and cerebellum | Ins2, insulin 2 (rat) | Pancreatic beta cells |
| Aqp2, aquaporin 2 (mouse) | kidney cells (collecting duct) and testes (sperm) | Ddx4, DEAD (Asp-Glu-Ala-Asp) box polypeptide 4 (mouse) | male and female germ cells starting at embryonic day (e)15-e18 | Itgax, integrin alpha X (mouse) | Dendritic cells |
| Atoh1, atonal homolog 1 (Drosophila) (mouse) | neural progenitors of the cerebellar rhombic lip, dorsal hindbrain and spinal cord, as well as in inner-ear primordia (with a limited amount of ectopic expression in the primordium of the hippocampus but not the cortex) | Emx1, empty spiracles homolog 1 (Drosophila) (mouse) | neurons of the neocortex and hippocampus | KRT14, keratin 14 (human) | skin, the oral ectoderm including the dental lamina at 11.75 d.p.c., and the dental epithelium by 14.5 d.p.c. |
| Camk2a, calcium/ calmodulin-dependent protein kinase II alpha (mouse) | forebrain; pyramidal cell layer | En1, engrailed 1 (mouse) | Spinal cord V1 interneurons, the embryonic mesencephalon and rhombomere 1 by E9, as well as in the ventral ectoderm of the limbs, in a subset of somite cells, and some mesoderm-derived tissues | Lck, lymphocyte protein tyrosine kinase (mouse) | thymocytes |
| Cartpt, CART prepropeptide (mouse) | cortex, hippocampus, and cerebellum | En2, engrailed 2 (mouse) | developing mesencephalon, rhombomere 1, and jaw muscles, as well as the embryonic and adult cerebellum | Lepr, leptin receptor (mouse) | hypothalmus (arcuate, dorsomedial, lateral, and ventromedial nuclei), limbic and cortical brain regions (basolateral amygdaloid nucleus, piriform cortex, and lateral entorhinal cortex), and retrosplenial cortex |
| Cd19, CD19 antigen (mouse) | B cells | Eno2, enolase 2, gamma, neuronal (rat) | neurons in many tissue types | Lgr5, leucine rich repeat containing G protein coupled receptor 5 (mouse) | crypt base columnar cells in small intestine (stem cells of the small intestine) and colon |

TABLE 1-continued

Nonlimiting exemplary cell-specific promoters

| Promoter | Cell/tissue specificity | Promoter | Cell/tissue specificity | Promoter | Cell/tissue specificity |
|---|---|---|---|---|---|
| Cdh5, cadherin 5 (mouse) | Embryonic and adult expression in endothelium of developing and quiescent vessels of all organs examined, as well as within a subset of hematopoietic cells | Fabp4, fatty acid binding protein 4, adipocyte (mouse) | Adipose tissue | Lyz2, lysozyme 2 (mouse) | myeloid cells—including monocytes, mature macrophages, and granulocytes |
| Cga, glycoprotein hormones, alpha subunit (mouse) | anterior and intermediate lobes of the pituitary gland, as well as in cardiac and skeletal muscle; low to no level of expression is detected in the posterior pituitary, lungs, kidneys, brain, adrenal gland and gonads | Foxg1, forkhead box G1 (mouse) | telencephalon, anterior optic vesicle (developing lens and retina), otic vesicle, facial and head ectoderm, olfactory epithelium, mid-hindbrain junction and pharyngeal pouches | Meox2, mesenchyme homeobox 2 (mouse) | epiblast-derived tissues as early as embryonic day 5; all primitive ectoderm by embryonic day 7 (but not endoderm or trophectoderm) |
| Chat, choline acetyltransferase (mouse) | cholinergic neurons | Foxp3, forkhead box P3 (mouse) | $Cd4^+Cd25^{high}Cd127^{low}$ T cells from the lymph nodes, spleen and thymus | Mnx1, motor neuron and pancreas homeobox 1 (mouse) | Motor neurons |
| Ckm, creatine kinase, muscle (mouse) | skeletal and cardiac muscle | GFAP, glial fibrillary acidic protein (human) | primarily in the central nervous system, affecting astrocytes, oligodendroglia, ependyma and some neurons; also periportal cells of the liver | Mybpcl, myosin binding protein C, slow-type (mouse) | cortex and hippocampus |
| Myf5, myogenic factor 5 (mouse) | Skeletal muscle and dermis | Myh11, myosin, heavy polypeptide 11, smooth muscle (mouse) | vascular and nonvascular smooth muscle | Myh6, myosin, heavy polypeptide 6, cardiac muscle, alpha, murine (murine) | heart |
| Nefl, neurofilament, light polypeptide (mouse) | Projection neurons | Nes, nestin (rat) | central and peripheral nervous system by embryonic day 11 and a few isolated kidney and heart cells | Neurog1, neurogenin 1 (mouse) | cortex, hippocampus, thalamus, hypothalamus and the cochlear-vestibular ganglion |
| Neurog3, neurogenin 3 (rat) | small intestine (base of intestinal crypts) and fetal pancreatic epithelial cells | Nkx2-1, NK2 homeobox 1 (mouse) | major subgroups of brain interneuron progenitors, developing lung, thyroid, and pituitary | Nr5a1, nuclear receptor subfamily 5, group A, member 1 (mouse) | in ventromedial hypothalamic nucleus, cerebral cortex, and a few scattered cells in the caudal brainstem, as well as in pituitary, gonad, and adrenal tissue |
| Olfr151, olfactory receptor 151 (mouse) | olfactory sensory neurons | Omp, olfactory marker protein (mouse) | mature olfactory sensory neurons | PTH, parathyroid hormone (human) | Parathyroid tissue |
| Pax3, paired box gene 3 (mouse) | dorsal neural tube and somites of embryonic day 9-11.5 embryos and in the cardiac neural crest cells and colonic epithelia of embryonic day 11.5 embryos | Pcp2, Purkinje cell protein 2 (L7) (mouse) | Purkinje cells | Pf4, platelet factor 4 (mouse) | megakaryocytes |
| Plp1, proteolipid protein (myelin) 1 (mouse) | oligodendrocytes and Schwann cells | Pomc, pro-opiomelanocortin-alpha (mouse) | arcuate nucleus of the hypothalamus and nucleus of the solitary tract in the hindbrain | Prm1, protamine 1 (mouse) | Male germ line |
| Prrx1, paired related homeobox 1 (rat) | early limb bud mesenchyme and in a subset of craniofacial mesenchyme, some female germline expression | Pvalb, parvalbumin (mouse) | most neurons that express parvalbumin including interneurons in the brain and proprioceptive afferent sensory neurons in the dorsal root ganglia | Rbp3, retinol binding protein 3, interstitial (rat) | Photoreceptor cells |
| Scnn1a, sodium channel, nonvoltage-gated 1 alpha (mouse) | cortex, striatum, hippocampus and cerebellum | Shh, sonic hedgehog (mouse) | Distal posterior region of the limb buds of embryos aged embryonic day 10 to 12 | Sim1, single-minded homolog 1 (Drosophila) (mouse) | paraventricular hypothalamus and other parts of the brain |

TABLE 1-continued

Nonlimiting exemplary cell-specific promoters

| Promoter | Cell/tissue specificity | Promoter | Cell/tissue specificity | Promoter | Cell/tissue specificity |
|---|---|---|---|---|---|
| Slc6a3, solute carrier family 6 (neurotransmitter transporter, dopamine), member 3 (mouse) | adult dopaminergic cell groups (substantia nigra (SN) and ventral tegmental area (VTA), as well as in the retrorubral field) | Togln, transgelin (mouse) | Vascular smooth muscle cells | Tek, endothelial-specific receptor tyrosine kinase (mouse) | female germline as well as tyrosine endothelial and hematopoietic cells |
| Th, tyrosine hydroxylase (rat) | Dopaminergic neurons | Thy1, thymus cell antigen 1, theta (mouse) | neurons of the postnatal cortex and hippocampus | Vil1, villin 1 (mouse) | Epithelial cells of the small and large intestines |
| Vsx2, visual system homeobox 2 (rat) | retina and Muller glial cells | Wap, whey acidic protein (mouse) | mammary gland tissues | Wfs1, Wolfram syndrome 1 homolog (human) (mouse) | cortex, hippocampus, striatum, thalamus and cerebellum |
| Wnt1, wingless-related MMTV integration site 1 (mouse) | embryonic neural tube, midbrain, dorsal and ventral midlines of the midbrain and caudal diencephalon, the mid-hindbrain junction and dorsal spinal cord | dlx6a, distal-less homeobox gene 6a, Danio rerio | GABAergic forebrain neurons | Vimentin | Mesenchymal cells |
| E-cadherin | Epithelial cells | | | | |

In some embodiments, a cell-specific promoter is a promoter that is active in plants. Many exemplary cell-specific plant promoters are known in the art. See, e.g., U.S. Pat. Nos. 5,097,025; 5,783,393; 5,880,330; 5,981,727; 7,557,264; 6,291,666; 7,132,526; and 7,323,622; and U.S. Publication Nos. 2010/0269226; 2007/0180580; 2005/0034192; and 2005/0086712, which are incorporated by reference herein in their entireties for any purpose.

Nonlimiting Exemplary Cell-Specific Exons

Many cell-specific exons are known in the art. Certain nonlimiting exemplary cell-specific exons are described in Table 2 and in the examples provided herein. The literature references provided in Table 2 are each incorporated by reference herein in their entireties for any purpose.

In some embodiments, a cell-specific exon is included in a selected cell. In some embodiments, the inclusion of the cell-specific exon allows for expression of an active product from a heterologous gene into which the exon is incorporated. In some embodiments, the inclusion of a cell-specific exon results in expression of an inactive product from a heterologous gene. In some embodiments, the inclusion of a cell-specific exon results in a decrease or elimination of expression of the heterologous gene product, for example, by inserting a stop codon upstream of the start codon of the heterologous gene and/or by frame-shifting the heterologous protein coding region.

In some embodiments, a cell-specific exon is excluded in a selected cell. In some embodiments, the exclusion of the cell-specific exon allows for expression of an active product from a heterologous gene into which the exon is incorporated. In some embodiments, the exclusion of a cell-specific exon results in expression of an inactive product from a heterologous gene. In some embodiments, the exclusion of a cell-specific exon results in a decrease or elimination of expression of the heterologous gene product, for example, by frame-shifting the heterologous gene coding region.

TABLE 2

Nonlimiting exemplary cell-specific exons

| Gene | Exon | Tissue specificity | Exemplary RNA elements | References |
|---|---|---|---|---|
| FGFR2 | IIIb | Epithelial | IAS2, ISAR, DICE | Oltean et al, 2008; Seth et al, 2008 and ref therein |
| FGFR2 | IIIc | Mesenchymal | IAS2, ISAR, DICE | Oltean et al, 2008; Seth et al, 2008 and ref therein |
| c-src | N1 | Neuronal | Fox2/KSRP, PTB/nPTB sites | Reviewed in Black, 2003. Originally identified in: Black, 1992; Chan and Black, 1995; Min et al, 1997; Chan and Black, 1997 |

TABLE 2-continued

Nonlimiting exemplary cell-specific exons

| Gene | Exon | Tissue specificity | Exemplary RNA elements | References |
|---|---|---|---|---|
| cardiac troponin T | Exon 5 | Embryonic muscle | Muscle specific enhancers | Ladd et al., 2001 and ref therein |
| Smarcc2, Ptprf, Brd9, Map4, Ank3 | Smarcc2 exon 16a, Ptprf exon 6a, Brd9 exon 5, Map4 exon 18, Ank3 exon 31a | Neuronal | Nova-1 and Nova-2 sites aka YCAY clusters | Ule et al., 2006 |
| Cardiac troponin T, insulin receptor, muscle specific chlorine channel, etc | Cardiac troponin T exon 5, insulin receptor exon 11, chloride channel intron 2 and exon 7a | Cardiac troponin T in heart, rest in skeletal muscle | CUGBP sites | Reviewed in Ranum and Cooper, 2006. Originally identified in, respectively, Phillips et al., 1998; Savkur et al.; Carlet et al., 2002 & Mankodi et al., 2002 |
| Fibronectin | ED I | TGF-B, injury to epithelial cells | GAAGAAGAC | Kornblihtt et al., 1996 and ref therein |
| Beta-tropomyosin | 6A and 6B | 6A in non-muscle and smooth muscle; 6B in skeletal muscle | G-rich enhancer | Gallego et al., 1996 and ref therein; Gooding et al., 2008 and ref therein |
| Enah | 11a | Epithelial | Fox2 and ESRP sites | Warzecha et al, 2009a and 2009b, and ref therein |
| Caspase 2, Slo K+ channel | Caspase 2 exon 9, Slo K+ channel STREX exon, | Central nervous system | Caspase 2: secondary structure region, Nova sites, (n)PTB sites; Slo K+ channel: Nova sites, (n)PTB sites | Barash et al., 2010 |
| PARD3, PTBP1, ENAH | Exons were not named, primers flanking are given: PARD3 cassette flanked by CCAGTTCTTGCTTTTCAACGA and TCCCCATTCAAAGTCACCTC, PTBP1 cassette flanked by AGAACATCTACAACGCCTGC and TCTGGGTTGAGGTTGCTGAC ENAH cassette flanked by: TGCTTCAGCCTGTCATAGTCA and TGGCAGCAAGTCACCTGTTA | Epithelial | Fox2 sites | Yeo et al., 2009 supplemental data |

Nonlimiting Exemplary Cell-Specific RNA Stability Elements

Various cell-specific RNA stability elements are known in the art. In some embodiments, a cell-specific RNA stability element is a microRNA target site. Many cell-specific microRNAs are known in the art. Nonlimiting exemplary mammalian cell-specific microRNAs are shown in Table 3.

In some embodiments, a cell-specific microRNA is a plant microRNA.

TABLE 3

Nonlimiting exemplary cell-specific microRNAs

| microRNA | Cell/tissue specificity | microRNA | Tissue specificity |
|---|---|---|---|
| miR-1a, d | heart | miR-122 | liver |
| miR-124a, b | brain | miR-219 | brain |
| Let-7c | midbrain | miR-154 | brain |
| miR-375 | Pancreatic islets | miR-125a, b | brain |
| miR-128a, b | brain | miR-127 | brain |
| miR-10a, b | Kidney | miR-218 | Brain |

TABLE 3-continued

Nonlimiting exemplary cell-specific microRNAs

| microRNA | Cell/tissue specificity | microRNA | Tissue specificity |
|---|---|---|---|
| miR-30a-3p | Kidney, lung, muscle | miR-204 | Brain |
| miR-148a | liver | miR-133a, b | Heart, muscle |
| miR-208 | Heart | miR-215 | Intestine |
| miR-194 | Intestine, kidney, liver | miR-31 | Intestine, liver |
| miR-141 | Intestine, kidney, lung | miR-10a | Intestine, kidney, lung, spleen |
| miR-150 | spleen | miR-142-5p, 3p | spleen |
| miR-126 | Endothelial cells | miR-155 | Hematopoietic cells |
| miR-142 | Hematopoietic cells | miR-181 | Hematopoietic cells |
| miR-223 | Hematopoietic cells | miR-140 | cartilage |
| miR-206 | muscle | | |

Nonlimiting Exemplary Constructs

In some embodiments, a construct for synthetic regulation of gene expression is provided. In some such embodiments, the construct comprises a cell-specific promoter and a cell-specific exon. In some embodiments, the construct further comprises a cell-specific RNA stability element.

In some embodiments, a construct may further contain one or more additional elements that facilitate the propagation, use, and/or functioning of the construct, such as, without limitation, one or more coding sequences for selectable markers, one or more origins of replication, localization domains, etc. Elements for use in constructs for in vitro and in vivo gene expression are known in the art, and one skilled in the art can select suitable elements to include in a construct for synthetic regulation of gene expression described herein. In some embodiments, the selected elements facilitate the propagation, use, and/or functioning of a construct in a mammal. In some embodiments, the selected elements facilitate propagation, use, and/or functioning of a construct in a plant. In some embodiments, an element facilitates propagation of a construct in vitro, although the construct is intended for use in vivo.

Nonlimiting Exemplary Methods

In some embodiments, methods of synthetic regulation of gene expression in a cell, mammal, or plant are provided. In some embodiments, methods of cell-specific expression of a gene in a cell, mammal, or plant are provided. In some embodiments, a method comprises introducing into a cell, mammal, plant, or introducing into a selected cell in a mammal or plant, a construct comprising a cell-specific promoter, a heterologous gene, and a cell-specific exon, under conditions allowing expression of the heterologous gene in the selected cell. In some embodiments, a construct further comprises a cell-specific RNA stability element.

In some embodiments, the heterologous gene is expressed in the selected cell at levels at least 2-fold, at least 3-fold, at least 4-fold, at least 5-fold, at least 6-fold, at least 7-fold, at least 8-fold, at least 9-fold, or at least 10-fold greater than it is expressed in one or more other cells of the same organism. In some embodiments, the heterologous gene is expressed in the selected cell at levels at least 2-fold, at least 3-fold, at least 4-fold, at least 5-fold, at least 6-fold, at least 7-fold, at least 8-fold, at least 9-fold, or at least 10-fold greater than it is expressed in other cells of the organism. In some embodiments, the heterologous gene is expressed in a set of selected cells at least 2-fold, at least 3-fold, at least 4-fold, at least 5-fold, at least 6-fold, at least 7-fold, at least 8-fold, at least 9-fold, or at least 10-fold greater than it is expressed in other cells of the organism. A set of selected cells may be any combination of cells in which a particular construct will express a heterologous gene. Nonlimiting exemplary sets of cells include, but are not limited to, cells of the cortex, hippocampus, and cerebellum; epithelial cells located in various tissues (such as kidneys and mammary glands); and muscle cells located throughout the body (such as skeletal muscle).

In some embodiments, a method comprises gene therapy in a mammal. In some such embodiments, the method allows expression of a heterologous gene in a selected cell type, with little or no expression of the heterologous gene in one or more other cell types. In some embodiments, a method comprises creating a transgenic animal. In some embodiments, a method comprises creating a transgenic plant. In some such embodiments, the method allows expression of a heterologous gene in a selected cell in the plant, with little or no expression of the heterologous gene in one or more other cells in the plant. In some embodiments, a method comprises creating transgenic fungi, for example, for temporal control of gene expression.

In some embodiments, the heterologous gene is expressed at a higher level in a selected cell and/or is expressed at a lower level in one or more other cells, than it would be expressed if it were only under the control of a cell-specific promoter.

The following examples are illustrative and are not intended to limit the claimed and/or disclosed subject matter.

EXAMPLES

Example 1: Synthetic Regulation of Gene Expression in Mesenchymal and Epithelial Cells To demonstrate synthetic regulation of gene expression, a set of plasmids was designed that would provide differential expression of firefly luciferase in mesenchymal and epithelial cells. As shown in FIG. 1A, four plasmids were designed. The control plasmid, pFFint, contains a firefly luciferase gene with a single intron that is spliced in both mesenchymal and epithelial cells, under the control of a CMV promoter, which is also active in both mesenchymal and epithelial cells. Plasmid pFFIIIc also contains a firefly luciferase gene under the control of a CMV promoter, but the gene contains the FGFR2 exon IIIc, which is efficiently spliced out in epithelial cells, but included in mesenchymal cells, resulting in an interruption of the luciferase open reading frame. Plasmid pE-Cad FFint contains a firefly luciferase gene with a single constitutive intron that is spliced in both mesenchymal and epithelial cells, but is under the control of the E-cadherin promoter, which is more active in epithelial cells than mesenchymal cells. Plasmid pE-cad-FFIIIc contains a firefly luciferase gene with the regulated FGFR2 exon IIIc, under the control of the E-cadherin promoter.

Mesenchymal-like rat prostate cancer cells, AT3 cells, and epithelial-like rat prostate cancer cells, DT cells, were grown (separately) in 6-well plates overnight in low glucose DMEM. DT and AT3 cells are described, for example, in Tennant et al. (2000). Each type of cell was transfected with 50 ng of each of the plasmids shown in FIG. 1A, along with 10 ng of a constitutive renilla luciferase as a transfection control, and 1.95 µg pUC19 as carrier DNA. The cells were incubated at 37° C. overnight following transfection. The cells were then lysed and lysates were cleared by centrifuging for 10 minutes at 20,000 rcf (relative centrifugal force, or xg) at 4° C. Luciferase activities in the cell lysates were determined using the Dual Luciferase Assay System (Promega, Madison, Wis.). The firefly signal was divided by the control renilla signal for each plasmid/cell combination.

Figure 1B:
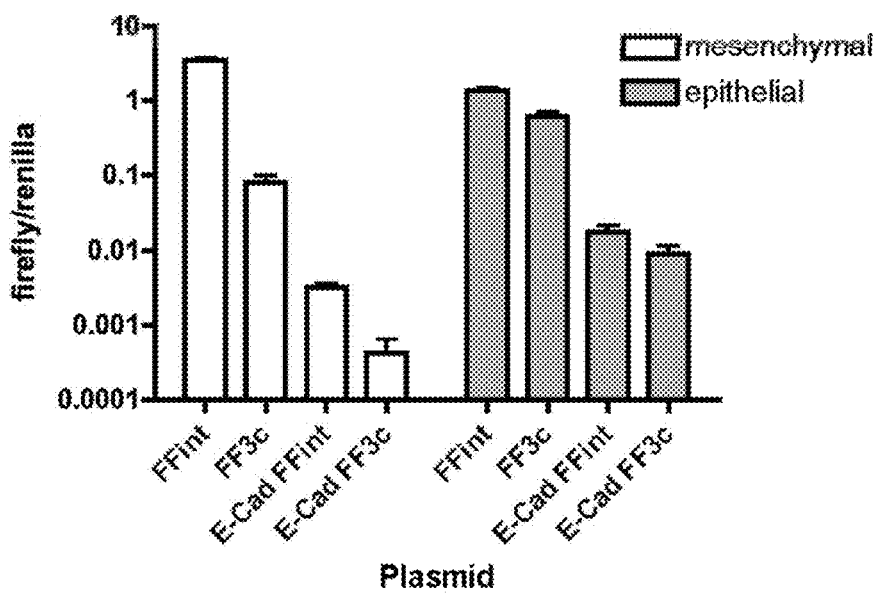

The results of that experiment are shown in FIG. 1B. Similar firefly luciferase activities were observed for mesenchymal and epithelial cells transfected with control plasmid FFint. Firefly luciferase expression was higher in epithelial cells than in mesenchymal cells transfected with either plasmid FFIIIc ("FF3c" in FIG. 1B) or plasmid E-Cad FFint. The greatest expression difference was provided by plasmid E-Cad FFIIIc ("E-Cad FF3c" in FIG. 1B), which contains both an epithelial-specific splicing cis-acting elements and an epithelial-specific promoter. These results demonstrate that by providing two levels of control, such as a cell-specific promoter and a cell-specific intron, greater expression differentials between cell types can be obtained.

Figure 2A:
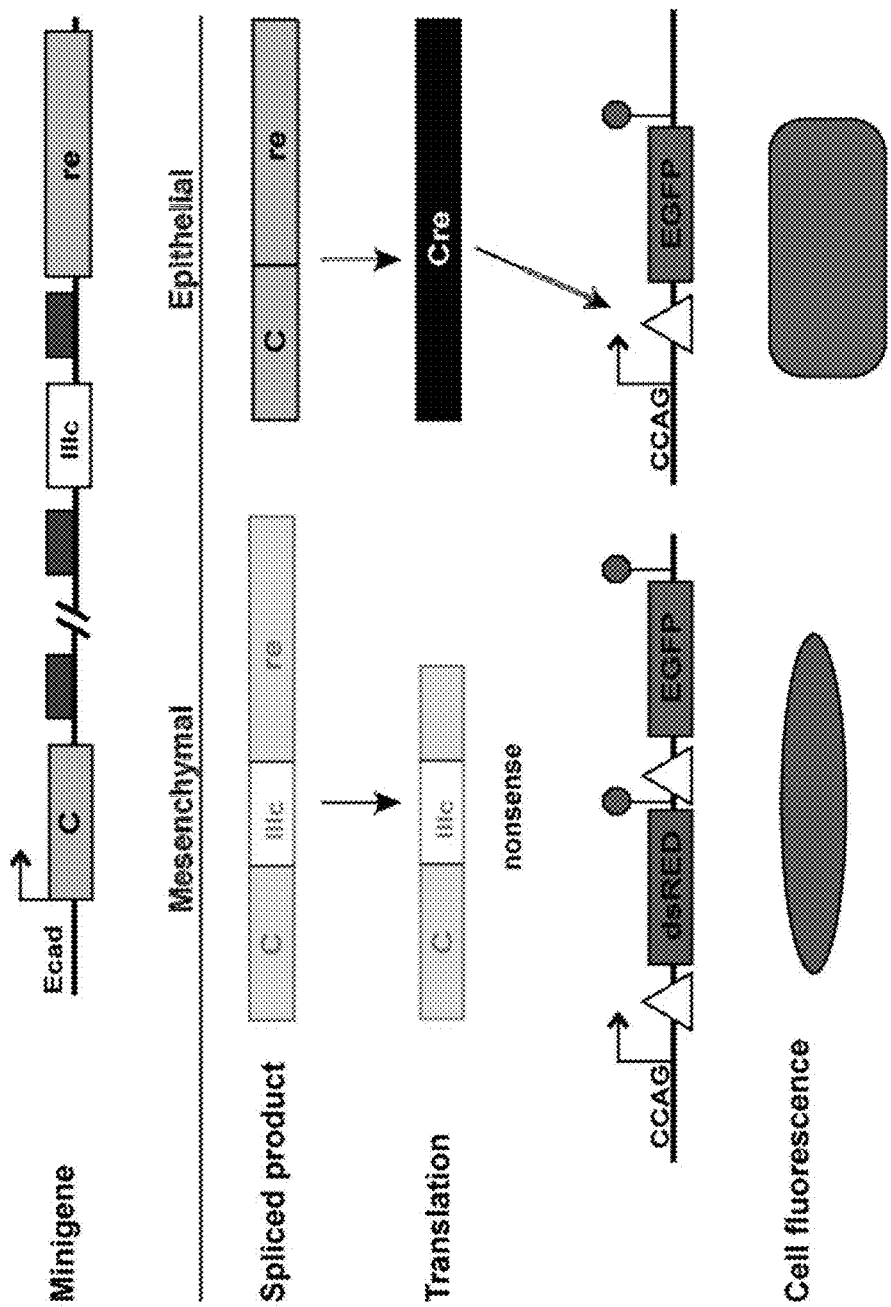
FIG. 2 shows in FIG. 2A a schematic diagram of a plasmid designed for epithelial-cell specific expression of Cre recombinase (Cre), and the predicted spliced products and translation products resulting from that plasmid in mesenchymal and epithelial cells, and a second plasmid that expresses dsRED in the absence of Cre protein and EGFP in the presence of Cre protein.
FIG. 2B shows fields of mesenchymal and epithelial cells transfected with the plasmids from FIG. 2A, showing expression of dsRED (left panels) and EGFP (right panels)
FIG. 2C shows quantitation of EGFP expression in mesenchymal and epithelial cells transfected with the plasmids from FIG. 2A over time, as described in Example 2.

Example 2: Synthetic Regulation of Gene Expression in Mesenchymal and Epithelial Cells Using a Cre/Lox System A system was designed to provide synthetic regulation of Cre expression in mesenchymal and epithelial cells, which would lead to a color change from red to green predominantly in epithelial cells. FIG. 2A shows the E-cadCreIIIc plasmid, which contains a Cre gene with the FGFR2 exon IIIc, under the control of the E-cadherin promoter. In mesenchymal cells, an inactive Cre fusion with FGFR2 exon IIIc will be expressed, which in epithelial cells, the FGFR2 exon IIIc will be spliced out and an active Cre protein will be expressed. The RG plasmid is also shown, which contains a dsRED gene flanked by loxP sites, followed by an EGFP gene. If an active Cre is produced in the cells, the dsRED gene will be removed, and the cells will express EGFP and be green. If an active Cre is not produced, the cells will express dsRED only and be red. The red circles in the RG plasmid indicated stop codons.

AT3 cells were transfected with 250 ng RG plasmid, 250 ng EcadCreIIIc plasmid, and 1.5 μg pUC19 as carrier DNA using lipofectamine (Invitrogen, Carlsbad, Calif.) according to the manufacturer's instructions. Dt cells were transfected with 100 ng RG plasmid, 100 ng EcadCreIIIc plasmid, and 1.8 μg pUC19 as carrier DNA also using lipofectamine according to the manufacturer's instructions. The cells were incubated at 37° C. overnight.

Figure 2B:
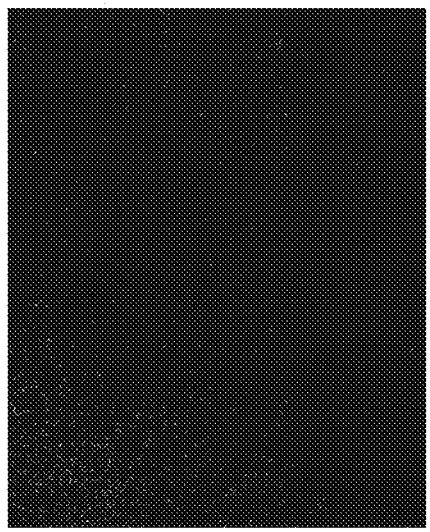
Figure 2B:
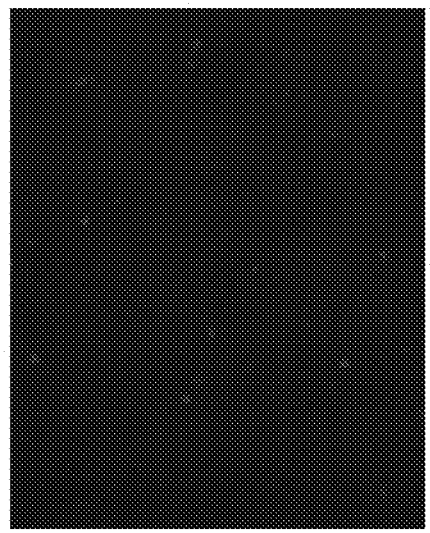
Figure 2B:
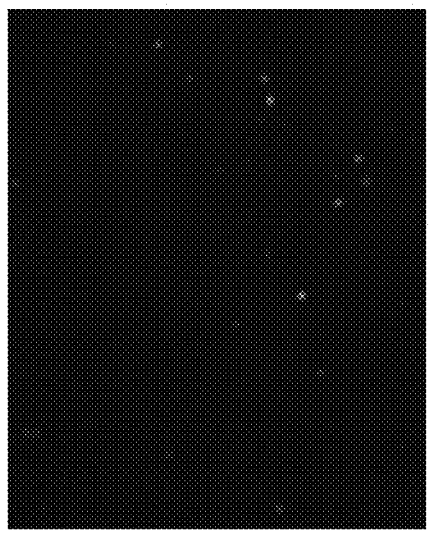
Figure 2B:
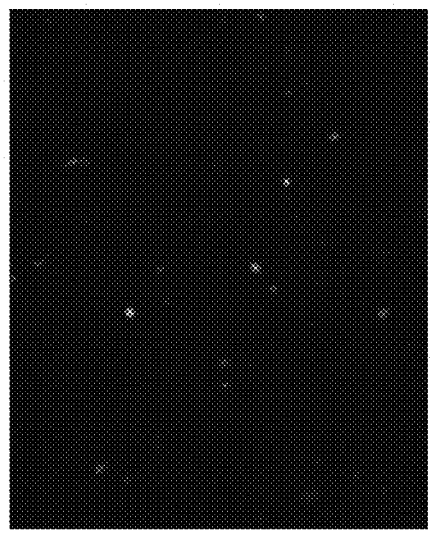

FIG. 2B is a picture of the red channel (left panels) and green channel (right panels) of transfected mesenchymal (top panels) and epithelial cells (bottom panels). Green cells were detected in the epithelial cell field, but not in the mesenchymal cell field.

The fraction of EGFP-positive cells was then tracked over time during selection for stable transfectants using hygromycin (selecting for the RG plasmid) and blastocidin (selecting for the EcadCreIIIc plasmid). Those results are shown in FIG. 2C. At all time points except one, only epithelial cells expressed detectable EGFP. These results suggest that the combination of the E-cadherin promoter and FGFR2 exon IIIc effectively limited Cre expression to epithelial cells.

Example 3: Synthetic Regulation of Toxin Expression

Figure 3A:
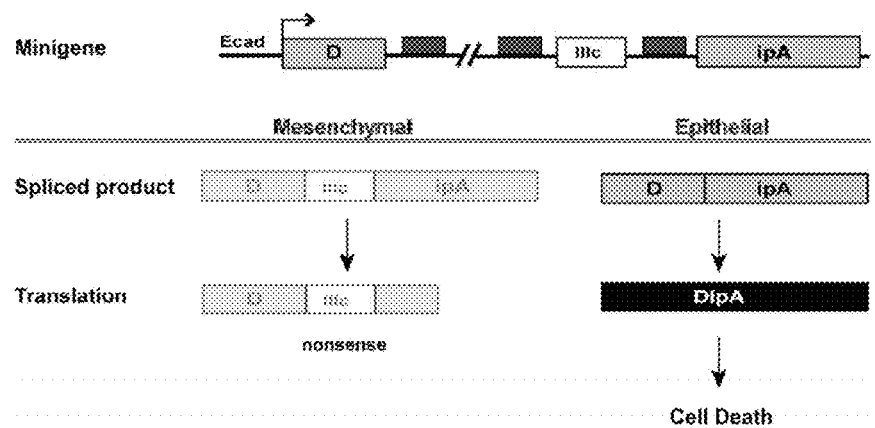
FIG. 3 shows in FIG. 3A a schematic diagram of a plasmid designed for epithelial cell-specific expression of diphtheria toxin, and the predicted spliced products and translation products resulting from that plasmid in mesenchymal and epithelial cells; and in FIG. 3B detection of transcripts resulting from the plasmid from FIG. 3A in transfected mesenchymal and epithelial cells, as described in Example 3.
Figure 3B:
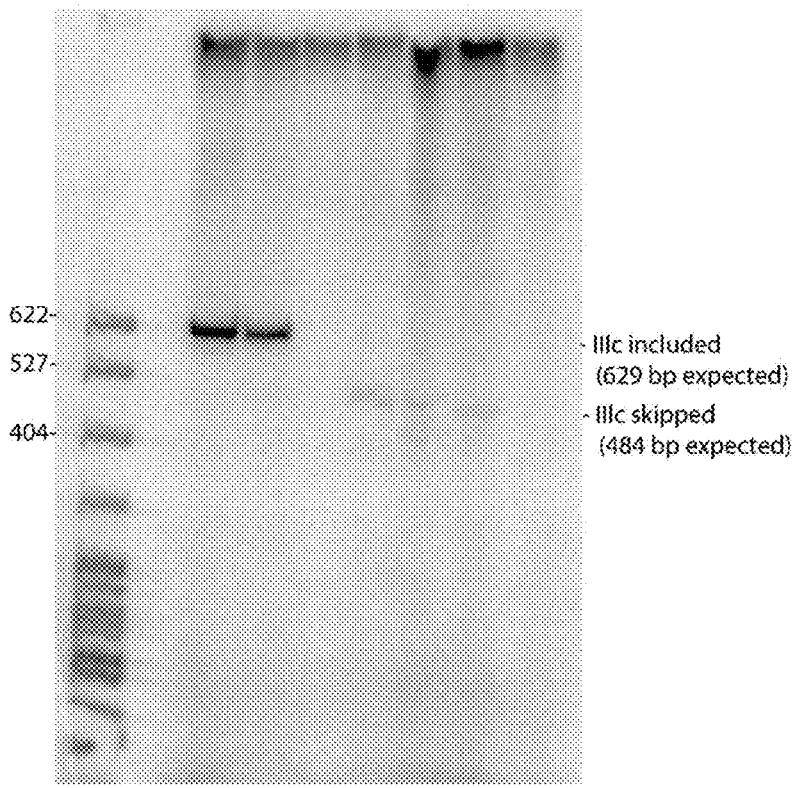

To determine whether the synthetic regulation systems discussed herein can be used to limit toxin expression to particular cell types, a plasmid was designed to express diphtheria toxin only in epithelial cells. FIG. 3A shows plasmid EcadDipIIIc, which contains a diphtheria toxin gene with an FGFR2 exon IIIc within the coding region, under the control of the E cadherin promoter. In mesenchymal cells, little transcript will be expressed, and the transcript that is expressed should retain the FGFR2 IIIc exon, resulting in an inactive protein product. In epithelial cells, the transcript is more strongly expressed, and the FGFR2 exon IIIc is skipped, resulting in active diphtheria toxin protein expression and cell death.

AT3 cells were transfected with 200 or 2,000 ng CMV-DipIIIc plasmid and 1.8 or 0 μg pUC19 as carrier DNA using lipofectamine (Invitrogen, Carlsbad, Calif.) according to the manufacturer's instructions. DT cells were transfected with 20 or 100 ng CMV-DipIIIc plasmid and 1.95 or 1.9 μg pUC19 as carrier DNA also using lipofectamine according to the manufacturer's instructions. The cells were incubated at 37° C. overnight with blasticidin selection, which selects for the CMV-DipIIIc plasmid. The presence or absence of the FGFR2 IIIc exon flanked by diphtheria toxin coding sequences was detected in mRNA isolated from the transfected cells using RT-PCR.

The results of that experiment are shown in FIG. 3B. In mesenchymal cells, exon IIIc was detected using diphtheria-specific primers, which little or no exon IIIc was detected in transcripts from epithelial cells, as would be expected. Little or no transcript lacking exon IIIc (and therefore encoding active diphtheria toxin) was detected in epithelial cells, suggesting that the cells that expressed the correctly spliced diphtheria toxin were killed. While not intending to be bound by any particular theory, the surviving epithelial cells may have eliminated the diphtheria toxin-expressing plasmid, may not express the transcript at all, and/or may express a defective diphtheria toxin protein. It should also be noted that transfection efficiency could not be controlled in this experiment.

Example 4: Mesenchymal-Specific Synthetic Regulation of Expression

A mesenchymal-specific expression vector was created using a vimentin promoter and by including FGFR2 exons IIIb and IIIc. Exon IIIb is skipped in mesenchymal cells, while exon IIIc is retained. A diagram of the vector is shown in FIG. 4A. The vector is shown in the center, with the various splice products shown above and below and labeled i, ii, iii, and iv. Splice product i results from excision of both exons IIIb and IIIc, and causes a frameshift in exemplary open reading frame (ORF) x and an inactive product. Splice product ii results from inclusion of exon IIIb and excision of exon IIIc (e.g., in epithelial cells), and results in a transcript with a stop codon ahead of ORF x. Splice product iii results from inclusion of both exons IIIb and IIIc, and results in a stop codon ahead of ORF x. Splice product iv results from exclusion of exon IIIb and inclusion of exon IIIc, resulting in a fusion of exon IIIc and ORF x in the correct reading frame and an active x fusion protein. Nonlimiting exemplary ORF x include luciferase, GFP, RFP, Cre, and DipA.

AT3 cells grown for one day in 6-well plates were transfected with 250 ng VimIIIbIIIc plasmid and 1.75 μg pUC19 as carrier DNA using lipofectamine (Invitrogen, Carlsbad, Calif.) according to the manufacturer's instructions. Dt cells were transfected with 250 ng VimIIIbIIIc plasmid and 1.75 μg pUC19 as carrier DNA also using lipofectamine according to the manufacturer's instructions. The cells were incubated at 37° C. overnight in low glucose DMEM. RNA was extracted from the cells using RNeasy (Qiagen) and the various splice products amplified by RT-PCR as previously described. See, e.g., Baraniak et al., *Mol.*

Cell Biol. 2006 February; 26(4):1209-22. The amplified products were then cleaved using AvaI or HincII, which cleave the four splice products in such a way that products of various sizes can be used to identify each of the four splice products. Uncut RT-PCT products separate into a longer band, which corresponds to inclusion of both exons IIIb and IIIc ("double inclusion"), and a shorter band, which corresponds to inclusion of either exon IIIb or IIIc ("single inclusion"). AvaI cleaves once in the IIIb exon. HincII cleaves twice in the IIIc exon. See, e.g., Carstens et al., *Mol. Cell Biol.*, 20(19): 7388-7400 (2000), which is incorporated by reference herein in its entirety for any purpose.

Figure 4A:
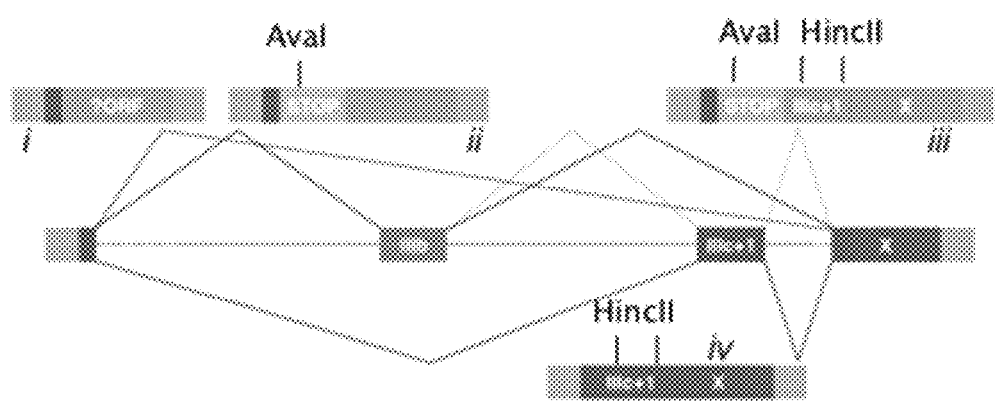
FIG. 4 shows in FIG. 4A a schematic diagram of a plasmid designed for mesenchymal cell-specific expression of a protein x, and four predicted spliced products resulting from that plasmid in mesenchymal and epithelial cells; and in FIG. 4B detection of transcripts resulting from the plasmid from FIG. 4A in transfected mesenchymal and epithelial cells, as described in Example 4.
Figure 4B:
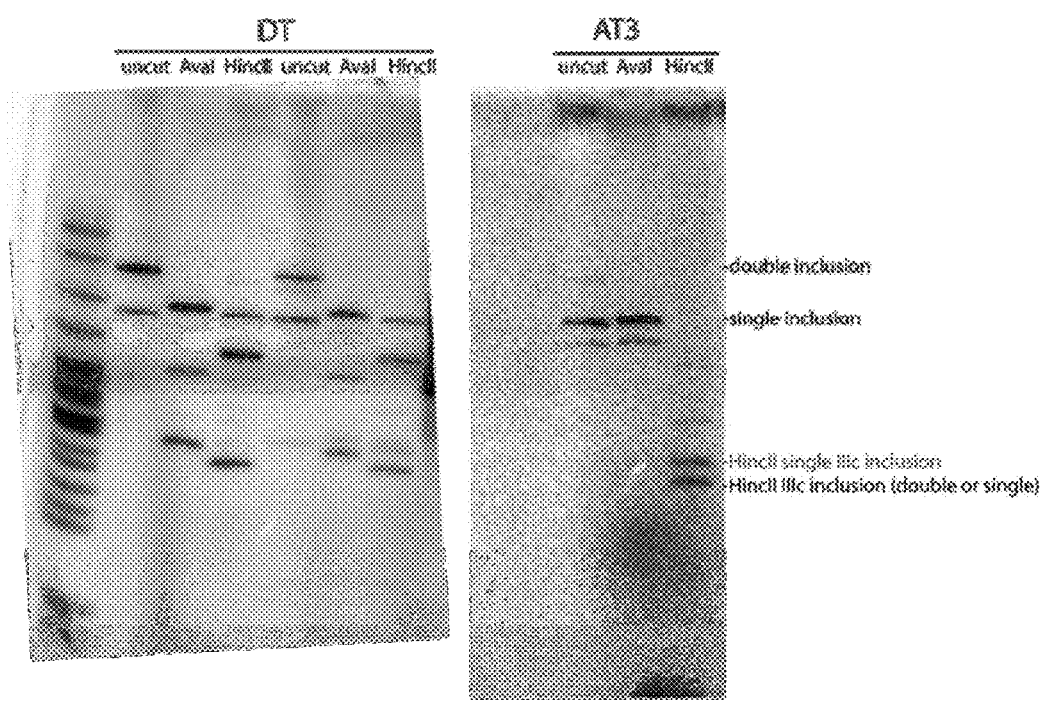

The results of that experiment are shown in FIG. 4B. The mesenchymal AT3 cells produced splice product iv, which includes exon IIIc only, whereas the epithelial DT cells did not produce appreciable levels of that splice product. Those results confirm that the VimxIIIbIIIc plasmid produces splice product iv, and presumably an active x fusion protein, in mesenchymal cells, but not epithelial cells. These results also demonstrate that changing the promoter from E-cadherin to vimentin does not affect the specificity of the splicing.

REFERENCES

Oltean et al., Clin Exp Metastasis. 2008; 25(6):611-9.
Seth et al., J Biol Chem. 2008 Apr. 11; 283(15):10058-67.
Black, Cell. 1992 May 29; 69(5):795-807.
Ladd et al., Mol Cell Biol. 2001 February; 21(4):1285-96.
Ule et al., Nature. 2006 Nov. 30; 444(7119):580-6.
Gallo et al., RNA Biol. 2010 July-August; 7(4):474-9.
Kornblihtt et al., FASEB J. 1996 February; 10(2):248-57.
Gallego et al., Biochimie. 1996; 78(6):457-65.
Gooding et al., Adv Exp Med Biol. 2008; 644:27-42.
Warzecha et al., RNA Biol. 2009 November-December; 6(5):546-62.
Warzecha et al., Mol Cell. 2009 Mar. 13; 33(5):591-601.
Barash et al., Bioinformatics. 2010 Jun. 15; 26(12):i325-33.
Yeo et al., Proc Natl Acad Sci USA. 2010 Nov. 30; 107(48):20715-9.
Black, Annu Rev Biochem. 2003; 72:291-336.
Tennant et al., Prostate. 2000 Jun. 1; 43(4):295-302.
Baraniak et al., Mol Cell Biol. 2006 February; 26(4):1209-22.
Carstens et al., Mol. Cell Biol. 2000 October; 20(19):7388-7400.

The invention claimed is:

1. A synthetic regulatory construct comprising a cell-specific promoter in operable communication with a heterologous gene and a cell-specific exon, wherein the cell-specific promoter and the cell-specific exon are obtained from two distinct genes, and wherein the cell-specific promoter and the cell-specific exon are specific for the same cell type or different cell types.

2. The construct of claim 1, wherein the cell-specific exon is excluded from a mature RNA encoding the heterologous gene in the cell type in which the cell-specific promoter is most active.

3. The construct of claim 2, wherein inclusion of the exon results in the product of the heterologous gene being inactive, or no product of the heterologous gene being produced.

4. The construct of claim 3, wherein inclusion of the exon results in a frame shift in the heterologous gene or a stop codon before or within the heterologous gene, or both.

5. The construct of claim 1, wherein the cell-specific exon is included in a mature RNA encoding the heterologous gene in the cell type in which the cell-specific promoter is most active.

6. The construct of claim 5, wherein exclusion of the exon results in the product of the heterologous gene being inactive, or no product of the heterologous gene being produced.

7. The construct of claim 6, wherein exclusion of the exon results in a frame shift in the heterologous gene or a stop codon before or within the heterologous gene, or both.

8. The construct of claim 1, wherein the construct further comprises a cell-specific RNA stability element.

9. The construct of claim 8, wherein the cell-specific RNA stability element is a microRNA target sequence.

10. An isolated cell comprising the construct of claim 1.

11. The cell of claim 10, wherein the cell is an animal cell or a plant cell.

12. A method of expressing a heterologous gene in a selected cell comprising: (a) introducing the synthetic regulatory construct of claim 1 into the selected cell; (b) inducing the cell-specific promoter within the synthetic regulatory construct in the cell to produce a pre-mRNA transcript comprising mRNA from the cell-specific exon and mRNA from the heterologous gene, wherein the pre-mRNA transcript is processed to a final mRNA transcript, and wherein the mRNA from the cell-specific exon is included in the final mRNA transcript through alternative splicing; and (c) expressing the heterologous gene if the mRNA from the cell-specific exon is included in the final mRNA transcript.

13. The method of claim 12, wherein the selected cell is selected from an animal cell, a plant cell and a fungal cell.

14. The method of claim 13, wherein the animal cell is from an animal selected from human, mouse, rat, dog, chimpanzee, and monkey.

15. The method of claim 13, wherein the selected cell is comprised in a non-human mammal or in a plant.

16. The method of claim 12, wherein the selected cell is selected from a mesenchymal cell, an epithelial cell, a neuronal cell, a heart muscle cell, a skeletal muscle cell, a smooth muscle cell, and an embryonic muscle cell.

17. The method of claim 12, wherein the product of the heterologous gene in inactive or not produced if the mRNA from the cell-specific exon is excluded from the final mRNA transcript.

18. The method of claim 12, wherein exclusion of the exon results in a frame shift in the heterologous gene or a stop codon before or within the heterologous gene, or both.

19. The method of claim 12, wherein the synthetic regulatory construct further comprises a cell-specific RNA stability element.

20. The method of claim 19, wherein the cell-specific RNA stability element is a microRNA target sequence.

21. The method of claim 12, wherein the cell-specific promoter is at least 2-fold, at least 3-fold, at least 5-fold, at least 7-fold, or at least 10-fold more active in the selected cell than in at least one other cell from the same organism as the selected cell.

22. The method of claim 12, wherein the cell-specific promoter is at least 2-fold, at least 3-fold, at least 5-fold, at least 7-fold, or at least 10-fold more active in the selected cell than in any other cell from the same organism as the selected cell.

* * * * *

SEQUENCE LISTING

```
<160> NUMBER OF SEQ ID NOS: 7

<210> SEQ ID NO 1
<211> LENGTH: 9
<212> TYPE: RNA
<213> ORGANISM: Homo sapiens

<400> SEQUENCE: 1 gaagaagac                                                              9

<210> SEQ ID NO 2
<211> LENGTH: 21
<212> TYPE: DNA
<213> ORGANISM: Artificial sequence
<220> FEATURE:
<223> OTHER INFORMATION: Synthetic

<400> SEQUENCE: 2
ccagttcttg cttttcaacg a                                                21

<210> SEQ ID NO 3
<211> LENGTH: 20
<212> TYPE: DNA
<213> ORGANISM: Artificial sequence
<220> FEATURE:
<223> OTHER INFORMATION: Synthetic

<400> SEQUENCE: 3
tccccattca aagtcacctc                                                  20

<210> SEQ ID NO 4
<211> LENGTH: 20
<212> TYPE: DNA
<213> ORGANISM: Artificial sequence
<220> FEATURE:
<223> OTHER INFORMATION: Synthetic

<400> SEQUENCE: 4
agaacatcta caacgcctgc                                                  20
```

```
<210> SEQ ID NO 5
<211> LENGTH: 20
<212> TYPE: DNA
<213> ORGANISM: Artificial sequence
<220> FEATURE:
<223> OTHER INFORMATION: Synthetic

<400> SEQUENCE: 5
tctgggttga ggttgctgac                                              20

<210> SEQ ID NO 6
<211> LENGTH: 21
<212> TYPE: DNA
<213> ORGANISM: Artificial sequence
<220> FEATURE:
<223> OTHER INFORMATION: Synthetic

<400> SEQUENCE: 6
tgcttcagcc tgtcatagtc a                                            21

<210> SEQ ID NO 7
<211> LENGTH: 20
<212> TYPE: DNA
<213> ORGANISM: Artificial sequence
<220> FEATURE:
<223> OTHER INFORMATION: Synthetic

<400> SEQUENCE: 7
tggcagcaag tcacctgtta                                              20
```